(12) United States Patent
Nishida et al.

(10) Patent No.: US 9,207,232 B2
(45) Date of Patent: Dec. 8, 2015

(54) CERAMIDE DERIVATIVE AND GOLGI APPARATUS-LABELING FLUORESCENT PROBE USING SAME (75) Inventors: Atsushi Nishida, Chiba (JP); Hiroyuki Nakamura, Chiba (JP); Tomohiko Makiyama, Chiba (JP); Toshihiko Murayama, Chiba (JP)

(73) Assignee: National University Corporation Chiba University (JP)

( * ) Notice: Subject to any disclaimer, the term of this patent is extended or adjusted under 35 U.S.C. 154(b) by 94 days.

(21) Appl. No.: 14/238,932

(22) PCT Filed: Aug. 13, 2012

(86) PCT No.: PCT/JP2012/070631
§ 371 (c)(1),
(2), (4) Date: Jun. 13, 2014

(87) PCT Pub. No.: WO2013/024843
PCT Pub. Date: Feb. 21, 2013

(65) Prior Publication Data
US 2014/0329266 A1  Nov. 6, 2014

(30) Foreign Application Priority Data
Aug. 15, 2011 (JP) ................................. 2011-177720

(51) Int. Cl.
| C12Q 1/02 | (2006.01) |
| G01N 33/50 | (2006.01) |
| G01N 33/58 | (2006.01) |
| C07D 271/12 | (2006.01) |
| G01N 33/92 | (2006.01) |

(52) U.S. Cl.
CPC .......... *G01N 33/5076* (2013.01); *C07D 271/12* (2013.01); *G01N 33/582* (2013.01); *G01N 33/92* (2013.01); *G01N 2405/08* (2013.01); *G01N 2500/10* (2013.01)

(58) Field of Classification Search
CPC . G01N 33/5076; G01N 33/582; G01N 33/92; G01N 2500/10; G01N 2405/08; C07D 271/12
See application file for complete search history.

(56) References Cited

FOREIGN PATENT DOCUMENTS
JP  2008-545724 A  12/2008

OTHER PUBLICATIONS

Makiyama et al. Eur. J. Pharmacol. (2012) 697: 144-151.*
Nussbaumer et al. Chem. Comm (2005) pp. 5086-5087.*
Hakogi, T. et al., Stereoselective synthesis of fluorescence-labeled sphingolipid, CSJ: The Chemical Society of Japan Koen Yokoshu, 2002, vol. 81, No. 2, p. 727, 3A2-50.
International Search Report issued for PCT/JP2012/070631 dated Sep. 18, 2012 (4 pages).
Lipsky, NG et al., A Vital Stain for the Golgi Apparatus, Science, 228, 745-747, 1985.
Makiyama, T. et al., Newly synthetic ceramide-1-phosphate analogs; their uptake, intracellular localization, and roles as an inhibitor of cytosolic phospholipase A2alpha and inducer of cell toxicity, Biochemical Pharmacology, 2010, vol. 80, pp. 1396-1406.

* cited by examiner

*Primary Examiner* — Susan Hanley
(74) *Attorney, Agent, or Firm* — Fox Rothschild LLP; Peter J. Butch, III; Robert N. Hernie, II (57) ABSTRACT A measure for selective fluorescent labeling of the Golgi apparatus, which has low cytotoxicity and excellent intracellular stability, is provided. According to the present invention, provided are a ceramide derivative represented by the following Chemical formula 1:

[Chemical formula 1]

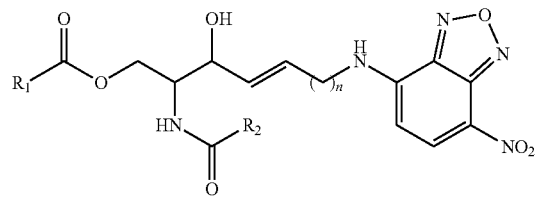

in the formula, $R_1$ is an alkyl group having 1 to 12 carbon atoms, $R_2$ is an alkyl group having 1 to 20 carbon atoms, and n is an integer of 1 to 20, and a Golgi apparatus-labeling fluorescent probe using the same.

18 Claims, 5 Drawing Sheets

CERAMIDE DERIVATIVE AND GOLGI APPARATUS-LABELING FLUORESCENT PROBE USING SAME

CROSS-REFERENCE TO RELATED APPLICATIONS

This application is a U.S. National Phase of international application PCT/JP2012/070631, filed Aug. 13, 2012, which claims priority to Japanese Patent Application No. 2011-177720, filed Aug. 15, 2011. The disclosures of both applications are incorporated herein by reference in their entirety.

TECHNICAL FIELD

The present invention relates to a ceramide derivative and a Golgi apparatus-labeling fluorescent probe using the same.

BACKGROUND ART

The Golgi apparatus is a cell organelle located in the center of the vesicular transport path, and present in most eukaryotic cells. The primary function of the Golgi apparatus is modification and sorting transport of proteins, and the Golgi apparatus is an important cell organelle that even performs synthesis of part of the lipids and glycolipids. In order that a protein functions properly, work of the Golgi apparatus is extremely important, and further 90% or more of sphingolipids which are important lipids in a living body is synthesized in the Golgi apparatus. As described above, it is extremely important in the understanding of the biological phenomena to study the function of the Golgi apparatus and a protein which functions in the Golgi apparatus.

By the way, in a study analyzing the intracellular transport of protein and lipid, and the protein that functions in the Golgi apparatus, it is frequently performed to observe the intracellular localization under a fluorescence microscope. At this time, it is also frequently performed to prove that the intended proteins are localized in the Golgi apparatus by the co-staining of a Golgi marker (Golgi apparatus-labeling probe) and the intended proteins. Therefore, it is extremely useful for the development of these studies to develop a Golgi apparatus-labeling probe which can selectively stain the Golgi apparatus.

Herein, for example, in Non Patent Literature 1, as a conventional Golgi apparatus-labeling fluorescent probe, a ceramide derivative which is referred to as a NBD-C6-ceramide is described. This NBD-C6-ceramide is obtained by the fluorescent labeling of the endogenous ceramide (N-acylsphingosine), and as shown in the following chemical structure, a fluorescent chromophore is substituted at the N-acyl site of ceramide. When introduced into a cell, due to such a chemical structure, the NBD-C6-ceramide is incorporated into the cell, and thus can selectively stain the Golgi apparatus.

CITATION LIST

Non Patent Literature

Non Patent Literature 1: N G Lipsky et al., Science, 228, 745-747, 1985

SUMMARY OF INVENTION

Technical Problem

However, according to the investigation by the present inventors, it was found that, in the staining of the Golgi apparatus using the above-described conventional ceramide derivative (NBD-C6-ceramide) as a fluorescent probe, there is a problem that the staining cannot be continuously performed over a long period of time. A NBD-C6-ceramide has a cytotoxic effect, therefore, kills a cell itself within 24 hours from the incorporation into the cell, and thus the cell observation cannot be continued anymore. Further, an endogenous ceramide is metabolized into a glucosylceramide by being added with an oligosaccharide in the Golgi apparatus, or metabolized into sphingomyelin by receiving the transfer of phosphocholine from phosphatidylcholine, as a result, the metabolite is sent to cell membrane and becomes a component of the cell membrane. The NBD-C6-ceramide is, in the same manner as in the endogenous ceramide, metabolized to glucosylceramide or sphingomyelin in the Golgi apparatus, and the metabolite is transported to cell membrane from the Golgi in a few hours, therefore, the continuous staining is also difficult in this respect.

Accordingly, an object of the present invention is to provide a measure for selective fluorescent labeling of the Golgi apparatus, which has low cytotoxicity and excellent intracellular stability.

Solution to Problem

The present inventors have conducted intensive studies in view of the above-described problems in the conventional technique. In the course, it was tried that in the NBD-C6-ceramide, the fluorescent chromophore that has been introduced at the N-acyl site of the endogenous ceramide (N-acylsphingosine) is introduced at the end of the alkyl group of a fatty acid instead of the N-acyl site, and further an acyl group is introduced at the end of the hydroxymethyl group of the endogenous ceramide. As a result, it was found that when the obtained compound is used as a fluorescent probe for the staining of the Golgi apparatus, the cytotoxicity is little shown, and further the intracellular stability is excellent.

According to the first aspect of the present invention, a ceramide derivative represented by the following Chemical formula 1:

(NMD-C6-ceramide)

[Chemical formula 1]

in the formula, $R_1$ is an alkyl group having 1 to 12 carbon atoms, $R_2$ is an alkyl group having 1 to 20 carbon atoms, and n is an integer of 1 to 20, is provided. The ceramide derivative is preferably represented by the following Chemical formula 2:

[Chemical formula 2]

in the formula, $R_1$, $R_2$, and n are the same as those in the above definition.

Further, in another preferable embodiment, $R_1$ is an alkyl group having 1 to 4 carbon atoms, $R_2$ is an alkyl group having 5 to 15 carbon atoms, and n is an integer of 7 to 11.

Furthermore, in the most preferable embodiment, the ceramide derivative is represented by the following Chemical formula 3:

[Chemical formula 3]

According to the second aspect of the present invention, a Golgi apparatus-labeling fluorescent probe containing the above-described ceramide derivative is provided.

According to the third aspect of the present invention, a method of identifying an existing site of the Golgi apparatus in a test cell is provided. The method includes: a step of bringing the above-described Golgi apparatus-labeling fluorescent probe into contact with a test cell; and a step of measuring a fluorescence signal emitted by the fluorescent probe.

According to the forth aspect of the present invention, a method of measuring the presence or absence, or a degree of the localization of a test compound to the Golgi apparatus in a test cell is also provided. The method includes: a step of bringing the above-described Golgi apparatus-labeling fluorescent probe into contact with a test cell; a step of measuring a fluorescence signal emitted by the fluorescent probe; a step of bringing a fluoresceinated test compound into contact with the test cell; and a step of measuring a fluorescence signal emitted by the test compound.

Advantageous Effects of Invention

According to the present invention, as a measure for selective fluorescent labeling of the Golgi apparatus, which has low cytotoxicity and excellent intracellular stability, a novel ceramide derivative, and a Golgi apparatus-labeling fluorescent probe using the same can be provided.

DESCRIPTION OF EMBODIMENTS

<<Ceramide Derivative>>

The first aspect of the present invention is a ceramide derivative represented by the following Chemical formula 1:

[Chemical formula 1]

As is apparent from the structure of the Chemical formula 1, the ceramide derivative according to the present aspect is obtained by the introduction of a fluorescent chromophore at the end of the alkyl group of a fatty acid instead of the N-acyl site of the endogenous ceramide (N-acylsphingosine), and further by the introduction of an acyl group ($R_1$—C(=O)—) at the end of the hydroxymethyl group of the endogenous ceramide.

In the Chemical formula 1, $R_1$ is an alkyl group having 1 to 12 carbon atoms. $R_1$ is preferably an alkyl group having 1 to 8 carbon atoms, more preferably an alkyl group having 1 to 4 carbon atoms, furthermore preferably methyl group or ethyl group, and particularly preferably methyl group. Herein, examples of the alkyl group having 1 to 12 carbon atoms include, for example, methyl group, ethyl group, n-propyl group, isopropyl group, n-butyl group, isobutyl group, sec-butyl group, tert-butyl group, aentyl group, hexyl group, heptyl group, octyl group, nonyl group, decyl group, undecyl group, and dodecyl group.

Further, in the Chemical formula 1, $R_2$ is an alkyl group having 1 to 20 carbon atoms. $R_2$ is preferably an alkyl group having 2 to 18 carbon atoms, more preferably an alkyl group having 3 to 17 carbon atoms, furthermore preferably an alkyl group having 4 to 16 carbon atoms, and particularly preferably an alkyl group having 5 to 15 carbon atoms.

Further, in the Chemical formula 1, n is an integer of 1 to 20. n is preferably 2 to 18, more preferably 3 to 16, furthermore preferably 4 to 14, still more preferably 5 to 13, particularly preferably 6 to 12, and most preferably 7 to 11.

A ceramide derivative represented by the Chemical formula 1 has two asymmetric carbon atoms. Specifically, the two asymmetric carbon atoms are the carbon atom ($C_A$) to which the nitrogen atom constituting the amide bond is bonded, and the carbon atom ($C_B$) which is adjacent to the carbon atom ($C_A$) and to which the hydroxyl group is bonded. The configuration of these asymmetric carbon atoms is not particularly limited. In other words, the configuration of $C_A$ and $C_B$, in the expression of ($C_A$, $C_B$), may be any one of (R, R), (R, S), (S, R), and (S, S). However, the configuration of ($C_A$, $C_B$) in the endogenous ceramide is (S, R), therefore, also in a ceramide derivative according to the present aspect, the configuration of ($C_A$, $C_B$) is particularly preferably (S, R). Among the ceramide derivatives represented by the Chemical formula 1, a ceramide derivative in which the configuration of ($C_A$, $C_B$) is (S, R) is represented by the following Chemical formula 2:

[Chemical formula 2]

Further, in the Chemical formula 2, $R_1$, $R_2$, and n are the same as those in the above definition.

Further, in the most preferable embodiment, a ceramide derivative according to the present aspect is represented by the following Chemical formula 3:

[Chemical formula 7]

[Chemical formula 3]

The acquisition route of the ceramide derivative described above is not particularly limited. Herein, an example of the techniques for the production of the ceramide derivative will be explained briefly, along with the synthetic scheme and Synthetic Example that will be described in the section of Examples below.

Firstly, in reference to the Synthesis Example 1, as a starting material, (S)-(−)-3-Boc-2,2-dimethyloxazolidine-4-carboxaldehyde (the following compound 1: commercially available from Aldrich Co.) is prepared. In the meantime, "-Boc" in the compound 1 is "tert-butoxycarbonyl group", which is a protecting group of the amine.

1

The acquisition route of the compound 1 is not particularly limited. As the compound 1, a commercial product may be purchased and used, or an own compound synthesized from a known starting material by a known reaction may be used.

Next, in the presence of a strong base such as n-BuLi, when a terminal alkyne is reacted with a compound 1, acetylide formed from the terminal alkyl by the action of the strong base performs a nucleophilic addition reaction to the carbonyl carbon of the aldehyde of the compound 1 (Reference: Renaud Villard, Djilali Hammache, Guillaume Delapierre,

Frédéric Fotiadu, Gérard Buono, JacquesFantini, Chem Bio Chem 2002, 3, 517-525). In the Synthesis Example 1, as the terminal alkyl, 1-hexyne is used, and thus the following compound 2 is obtained.

Next, in reference to the Synthesis Example 2, in the presence of a nucleophilic solvent such as methanol and ethanol, by the treatment of the above-obtained compound 2 with a weakly acidic cation-exchange resin (for example, Amberlyst (registered trademark) 15), an oxazolidine ring is opened, and thus a carbamate derivative such as the following compound 3 can be obtained.

Next, in reference to the Synthesis Example 3, by the treatment of the above-obtained compound 3 with a reducing agent (for example, hydrogenated bis(2-methoxyethoxy)sodium aluminum (Red-Al)), the triple bond is reduced to a double bond, and thus a carbamate derivative such as the following compound 4 can be obtained.

Next, in reference to the Synthesis Example 4, by heating and refluxing of the above-obtained compound 4 in the presence of a strong acid such as hydrochloric acid and trifluoroacetic acid, the Boc protecting group is released from the amino group (deprotection), and thus a diol compound such as the following compound 5 containing a primary amino group can be obtained.

Next, in reference to the Synthesis Example 5, by the reacting of the above-obtained compound 5 with a carboxylic acid chloride, a diol compound in which an amide bond is formed at the site of the primary amino group in the compound 5 can be obtained. Herein, by selecting the length of the alkyl group of the carboxylic acid chloride used in the reaction, $R_2$ in the compound 1 can be controlled. In the Synthesis Example 5, palmitoyl chloride is used as the carboxylic acid chloride, and thus the following compound 6 that corresponds to a compound in which $R_2$ in the Chemical formula 1 is pentadecyl group is obtained.

Next, in reference to the Synthesis Example 6, a fluorescent chromophore is introduced at the site of the alkenyl group in the above-obtained compound 6. Specifically, by reacting a compound obtained by substituting one of the hydrogen atoms of the primary amino group of the 7-nitro-2,1,3-benzoxadiazole-4-amine, which is a fluorescent compound, with a terminal alkenyl group (in the Synthesis Example 6, the following compound 7), with the compound 6 in the presence of the second generation Grubbs catalyst, which is a carbene complex catalyst, recombination of binding of two olefins occurs, and thus a fluorescent chromophore is introduced at the site of the alkenyl group of the compound 6. Herein, by selecting the length of the terminal alkenyl group described above, n in the compound 1 can be controlled. In the Synthesis Example 6, as the terminal alkenyl group, 10-undecenyl group is employed, and thus the following compound 8 that corresponds to a compound in which n in the Chemical formula 1 is 9 is obtained.

Finally, in reference to the Synthesis Example 7, by reacting of the above-obtained compound 8 with a carboxylic acid chloride under a low-temperature condition of around −15° C., an acyl group is bonded to the primary hydroxy group in the compound 8, and thus the synthesis of a ceramide derivative according to the present invention is completed. Herein, by the selection of the length of the alkyl group of the carboxylic acid chloride used in the reaction, $R_1$ in the compound 1 can be controlled. In the Synthesis Example 7, acetyl chloride is used as a carboxylic acid chloride, and thus the following compound 9 that corresponds to a compound in which R₁ in the Chemical formula 1 is methyl group is obtained.

A technique for the production of the ceramide derivative according to the first aspect was described above by using the compound 9 as an example. Of course, the ceramide derivative can be produced by other techniques, and the scope of the compound or the applications of the compound of the present invention is not affected by the production method.

<<Golgi Apparatus-Labeling Fluorescent Probe>>

The second aspect of the present invention is a Golgi apparatus-labeling fluorescent probe containing a ceramide derivative according to the above-described first aspect.

Conventionally, when a Golgi apparatus-labeling fluorescent probe (NBD-C6-ceramide) composed of a ceramide derivative which is described, for example, in Non Patent Literature and the like is used as a fluorescent probe to stain the Golgi apparatus, there has been a problem that the staining cannot be continuously performed over a long period of time. On the other hand, as demonstrated in the section of Examples below, when a ceramide derivative according to the first aspect is used as a Golgi apparatus-labeling fluorescent probe, an extremely significant effect that the cytotoxicity is low and the intracellular stability is excellent is exerted. Therefore, the Golgi apparatus-labeling fluorescent probe according to the second aspect can be an effective probe that contributes to the elucidation of a lipid metabolism mechanism in a cell, or the development of therapeutic drugs for the disease caused by a disorder of lipid metabolism.

Herein, it is not completely clear about the mechanism in which a ceramide derivative provided by the present invention exerts such an excellent effect as a Golgi apparatus-labeling fluorescent probe. About being excellent in the intracellular stability, as shown in the Chemical formula 1, the fluorescent chromophore is positioned at the end of the alkyl group of the fatty acid instead of the N-acyl site, therefore it is presumed that the color development of fluorescence is not affected even when the breakage (degradation) is generated by the metabolism. Further, as also shown in the Chemical formula 1, by the introduction of an acyl group (R₁—C(=O)—) at the end of the hydroxymethyl group of the endogenous ceramide, the metabolite is not recognized as a metabolic substrate for hydrolytic enzymes, and thus it is considered that the ceramide derivative contributes to the further improvement of the intracellular stability, and also leads to the decrease of the cytotoxicity.

The usage of a fluorescent probe according to the present invention is not particularly limited, and the probe may be used in the same manner as the conventionally known fluorescent probe. Usually, in an aqueous medium such as a saline solution, and a buffer solution, a mixture of a water-mixing organic solvent such as ethanol, acetone, ethylene glycol, dimethyl sulfoxide, and dimethylformamide, and an aqueous medium, or the like, the above-described ceramide derivative is dissolved, the solution thus obtained is added into an appropriate buffer solution containing an object to be tested such as a cell, and a tissue, and then the fluorescence intensity of the resultant solution may be measured by the excitation at a wavelength in the vicinity of 490 nm appropriately selected.

In addition, the fluorescent probe according to the present invention may be used in a form of a composition combined with an appropriate additive. For example, as the additive, an additive such as a buffer agent, and a solubilizer can be appropriately combined.

Herein, as the third aspect of the present invention, a method of identifying an existing site of the Golgi apparatus in a test cell is provided. The method includes: a step of bringing the above-described Golgi apparatus-labeling fluorescent probe into contact with a test cell; and a step of measuring a fluorescence signal emitted by the fluorescent probe. In the method, the kind, culture method, and the like of the test cell are not particularly limited, and conventionally known knowledge can be appropriately referred to. Further, the specific embodiment of bringing a fluorescent probe into contact with a test cell is not particularly limited, either. In addition, the term "measure" used in the present specification should be interpreted in the broadest meaning including quantitative, and qualitative.

Further, as the forth aspect of the present invention, a method of measuring the presence or absence, or a degree of the localization of a test compound to the Golgi apparatus in a test cell is also provided. The method includes: a step of bringing the above-described Golgi apparatus-labeling fluorescent probe into contact with a test cell; a step of measuring a fluorescence signal emitted by the fluorescent probe; a step of bringing a fluoresceinated test compound into contact with the test cell; and a step of measuring a fluorescence signal emitted by the test compound. Herein, for example, the above-described Golgi apparatus-labeling fluorescent probe, and the test compound are excited, and/or emitted, respectively at a different wavelength from each other, and thus by the observation of whether or not the localized site of the fluorescence emitted from each of the probe and the compound matches with each other, the presence or absence, or the degree of the localization of a test compound to the Golgi apparatus in a test cell can be measured.

In the step of measuring a fluorescence signal in the third aspect or the forth aspect of the present invention, for example, a measurement using a confocal laser scanning microscope, which is a measurement as used in the section of Examples below may be employed.

EXAMPLES

Hereinafter, the present invention will be described in more detail by way of Examples and the like, however, the technical scope of the present invention is not limited thereto.

SYNTHESIS EXAMPLES

According to the following synthetic scheme, the compound 9, which is a ceramide derivative according to the present invention was synthesized.

Synthetic scheme

Synthesis Example 1

Synthesis of tert-butyl (S)-4-((R)-1-hydroxyhept-2-yn-1-yl)-2,2-dimethyloxazolidine-3-carboxylate (Compound 2)

Under an argon atmosphere, into an anhydrous tetrahydrofuran (THF) (50 mL) solution of 1-hexyne (1.10 g, 13.08 mmol), a n-BuLi solution (7.7 mL, 12.21 mmol, 1.59 M (hexane solution)) was added dropwise at −20° C. The resultant mixture was stirred at −20° C. for two hours, and cooled to −78° C., then into which hexamethylphosphoic triamide (HMPA: 3 mL, 17.44 mmol) was added, and further a THF (37 mL) solution of (S)-(−)-3-Boc-2,2-dimethyloxazolidine-4-carboxaldehyde (compound 1: commercially available from Aldrich Co.) (2.0 g, 8.72 mmol) was added. The resultant mixture was stirred at −78° C. for one hour, and then heated to room temperature over two hours. The reaction was quenched by the addition of saturated aqueous solution of $NH_4Cl$, then the resultant reaction mixture was concentrated under reduced pressure, and into the residue, ether and water were added, and then the resultant mixture was separated. Further, the aqueous layer was extracted with ether, and the combined organic layer was dried over anhydrous sodium sulfate. The organic layer was concentrated under reduced pressure, then the obtained residue was purified by silica gel column chromatography (eluent: n-hexane/ethyl acetate (9/1)), and the compound 2 (2.36 g, 87%) was obtained as a colorless oil.

(Reference: Renaud Villard, Djilali Hammache, Guillaume Delapierre, Frédéric Fotiadu, Gérard Buono, Jacques-Fantini, Chem Bio Chem 2002, 3, 517-525).

Synthesis Example 2

Synthesis of tert-butyl((2S,3R)-1,3-dihydroquinone-4-yn-2-yl)carbamate (Compound 3)

Into a methanol solution (67 mL) of the compound 2 (2.08 g, 6.7 mmol) synthesized by the method of the Synthesis Example 1 described above, a weakly acidic ion exchange resin, Amberlyst (registered trademark) 15 (2.5 g) was added, and the resultant mixture was stirred at room temperature for 20 hours. The resultant reaction mixture was filtered through celite, then the filtrate was concentrated under reduced pressure, and thus a crude product was obtained. The crude product was purified by silica gel column chromatography (eluent: n-hexane/ethyl acetate (2/1)), and the compound 3 (1.5 g, 81%) was obtained as a colorless oil.

$^1$H NMR ($CDCl_3$, 400 MHz) δ; 0.91 (t, J=7.2 Hz, 3H), 1.36-1.53 (m, 13H), 2.23 (td, J=6.9, 2 Hz, 2H), 2.41 (br, 1H), 2.89 (br, 1H), 3.77 (m, 2H), 4.10 (m, 1H), 4.60 (br, 1H), 5.30 (br, 1H);

$^{13}$C NMR (CDCl$_3$, 400 MHz) δ; 13.5, 18.3, 21.9, 28.3, 30.5, 55.8, 62.7, 64.5, 77.9, 80.0, 87.9, 156.2;
IR (neat) υ: 3421, 2959, 2933, 2873, 1685, 1507 cm$^{-1}$;
[α]$_D^{26}$ –10.0 (c 0.5, CHCl$_3$).

Synthesis Example 3

Synthesis of tert-butyl((2S,3R)-(E)-1,3-dihydroquinone-4-en-2-yl)carbamate (Compound 4)

Into an ether solution (1.3 mL) of the compound 3 (100 mg, 0.37 mmol) synthesized by the method of the Synthesis Example 2 described above, Red-Al (registered trademark, 0.56 mL, 1.84 mmol, 65% toluene solution) was added dropwise at 0° C., and then the resultant mixture was stirred at room temperature for 10 hours. The reaction was quenched by the addition of methanol at 0° C., then into which ether (10 mL) and a saturated aqueous solution of potassium sodium tartrate were added, and the resultant mixture was vigorously stirred at room temperature for 12 hours. The product was extracted with ether, and further the extract was washed with a saturated aqueous solution of potassium sodium tartrate, and then with a saturated salt solution. The extract was dried over anhydrous magnesium sulfate, and then concentrated under reduced pressure. The obtained residue was purified by silica gel column chromatography (eluent: n-hexane/ethyl acetate (1/1)), and the compound 4 (82 mg, 82%) was obtained as a white solid.

$^1$H NMR (CDCl$_3$, 400 MHz) δ; 0.90 (t, J=6.8 Hz, 3H), 1.24-1.43 (m, 4H), 1.46 (s, 9H), 2.07 (q, J=6.7 Hz, 2H), 2.43 (br, 2H), 3.60 (br, 1H), 3.71 (ddd, J=11.2, 7.6, 3.6, 1H), 3.94 (dt, J=11.6, 4 Hz, 1H), 4.32 (br, 1H), 5.27 (br, 1H), 5.57 (dd, J=15.6, 6.4 Hz, 1H), 5.78 (dt, J=15.2, 7.2 Hz, 1H);
$^{13}$C NMR (CDCl$_3$, 400 MHz) δ; 13.8, 22.2, 28.3, 31.1, 31.9, 55.4, 62.6, 74.6, 79.8, 128.9, 134.0;
IR (neat) υ: 3394, 2958, 2929, 2873, 1684, 1507, 1365, 1165, 969 cm$^{-1}$;
[α]$_D^{18}$ –2.9 (c 0.5, CHCl$_3$);
LRMS (FAB) m/z 274 [M+H]$^+$, 296 [M+Na]$^+$;
HRMS (FAB) calcd for C$_{14}$H$_{27}$NO$_4$Na 296.1838 [M+Na]$^+$. found 296.1825.

Synthesis Example 4

Synthesis of (2S,3R)-(E)-2-aminonon-4-en-1,3-diol (Compound 5)

Into a THF solution (7.2 mL) of the compound 4 (200 mg, 0.73 mmol) synthesized by the method of the Synthesis Example 3 described above, 1N hydrochloric acid (2.4 mL) was added, then the resultant reaction mixture was heated to reflux for 23 hours, and cooled to room temperature after the confirmation of disappearance of the starting materials. Into the resultant reaction mixture, 1N aqueous sodium hydroxide solution (2.6 mL) and a saturated salt solution were added, and then the resultant mixture was extracted with ethyl acetate. The organic layer was dried over anhydrous magnesium sulfate, then concentrated under reduced pressure, and thus a crude product was obtained. The obtained crude product was purified by silica gel column chromatography (eluent: CHCl$_3$/methanol/NH$_4$OH (135/25/4)), and the compound 5 (120 mg, 94%) was obtained as a colorless oil.

$^1$H NMR (CDCl$_3$, 400 MHz) δ; 0.90 (t, J=7.0 Hz, 3H), 1.30-1.41 (m, 4H), 1.75 (br, 2H), 2.07 (q, J=6.7 Hz, 2H), 2.87 (q, J=5.3 Hz, 3H), 3.62 (dd, J=10.6, 6.2 Hz, 1H), 3.68 (dd, J=11, 4.6 Hz, 1H), 4.04 (t, J=6.2 Hz, 1H), 5.48 (dd, J=15.4, 7 Hz, 1H), 5.76 (dt, J=15.6, 6.8 Hz, 1H);

$^{13}$C NMR (CDCl$_3$, 400 MHz) δ: 13.8, 22.2, 31.3, 32.0, 56.2, 63.8, 75.1, 129.4, 134.5;
IR (neat) υ: 3355, 2956, 2925, 2872, 2857, 1459, 970 cm$^{-1}$;
LRMS (FAB) m/z 174 [M+H]$^+$ 196 [M+Na]$^+$.

Synthesis Example 5

Synthesis of N-((2S,3R)-(E)-1,3-dihydroxynone-4-en-2-yl)palmitamide (Compound 6)

Into a THF solution (10 mL) of the compound 5 (86.9 mg, 0.50 mmol) synthesized by the method of the Synthesis Example 4 described above, 5 mL of 50% aqueous solution of sodium acetate was added, then the resultant mixture was cooled to 0° C., and into the cooled mixture, palmitoyl chloride (330 μL, 1.08 mmol, 2.2 eq) was added. The resultant mixture was stirred at room temperature for 30 minutes, then into which water was added, and the resultant mixture was extracted with ethyl acetate. The organic layer was dried over anhydrous magnesium sulfate, then concentrated under reduced pressure, and thus a crude product was obtained. The obtained crude product was purified by silica gel column chromatography (eluent: CHCl$_3$/methanol (40/1)), and the compound 6 (204.8 mg, 99%) was obtained as a colorless oil.

$^1$H NMR (CDCl$_3$, 400 MHz) δ; 0.88 (t, J=7.2 Hz, 3H), 0.90 (t, J=7.2 Hz, 3H), 1.25-1.39 (m, 28H), 1.64 (quin, J=7.2 Hz, 2H), 2.07 (q, J=6.8 Hz, 2H), 2.23 (t, J=7.8 Hz, 2H), 2.60 (m, 2H), 3.71 (ddd, J=10.8, 7.4, 3.4 Hz, 1H), 3.91 (dt, J=11.2, 3.6 Hz, 1H), 3.95 (dt, J=11.2, 3.6 Hz, 1H), 4.33 (q, J=5.6 Hz, 1H), 5.54 (ddt, J=15.2, 6.8, 1.6 Hz, 1H), 5.79 (dtd, J=15.2, 6.8, 1.6 Hz, 1H), 6.22 (d, J=6.0 Hz, 1H);
$^{13}$C NMR (CDCl$_3$, 400 MHz) δ; 174.2, 133.9, 128.8, 74.0, 62.2, 54.6, 36.8, 35.9, 31.91, 31.86, 31.2, 29.64, 29.61, 29.5, 29.4, 29.3, 29.28, 29.2, 25.7, 25.5, 22.6, 22.2, 14.1, 13.8;
IR (neat) υ: 3285, 2953, 2916, 2849, 1644, 1557, 964 cm$^{-1}$;
[α]$_D^{18}$ –2.2 (c 1.0, CHCl$_3$);
LRMS (FAB) m/z 412 [M+H]$^+$, 434 [M+Na]$^+$;
HRMS (FAB) calcd for C$_{25}$H$_{49}$NO$_3$Na 434.3610 [M+Na]$^+$. found 434.3605.

Synthesis Example 6

Synthesis of N-((2S,3R)-(E)-1,3-dihydroxy-14-(7-nitrobenzo[c][1,2,5]oxadiazole-4-ylamino)tetradec-4-en-2-yl)palmitamide (Compound 8)

A CH$_2$Cl$_2$ (24 mL) solution of the compound 6 (100 mg, 0.24 mmol) synthesized by the method of the Synthesis Example 5 described above, and 7-nitrobenzo[c][1,2,5]oxadiazole-4-(10-undecenyl)amine (compound 7) (81 mg, 0.243 mmol) (P. Nussbaumer, P. Ettmayer, C. Peters, D. Rosenbeiger and K. Högenauer, Chem. Commun., 2005, 5086-5087) was bubbled with argon gas for one hour, then into the resultant mixture, the second generation Grubbs catalyst (5 mol %) was added, and the resultant mixture was heated to reflux for 4 hours. The solvent was distilled off under reduced pressure, then the residue was purified by silica gel column chromatography (Fuji Silysia NH Silica, eluent: n-hexane/ethyl acetate (1/2)), and the compound 8 (60 mg, 37%) was obtained, thus 33 mg (33%) of the compound 6, which is a raw material was recovered.

$^1$H NMR (CDCl$_3$, 55° C., 400 MHz) δ; 0.88 (t, J=6.6 Hz, 3H), 1.25-1.37 (m, 34H), 1.47 (quin, J=7.4 Hz, 2H), 1.63 (quin, J=7.3 Hz, 2H), 1.81 (quin, J=7.2 Hz, 2H), 2.04 (dt, J=6.8, 6.8 Hz, 2H), 2.23 (t, J=7.6 Hz, 2H), 2.85-3.05. (br, 2H), 3.5 (dt, J=13.2, 6.8 Hz, 1H), 3.71 (br, 1H), 3.9 (m, 1H), 4.3 (br, 1H), 5.55 (dd, J=15.6, 6.4 Hz, 1H), 5.76 (dt, J=15.6, 6.8 Hz, 1H), 6.16 (d, J=8.8 Hz, 1H), 6.27 (d, J=6.0 Hz, 1H), 6.60 (br, 1H), 8.45 (d, J=8.8 Hz, 1H);

$^{13}$C NMR (CDCl$_3$, 55° C., 400 MHz) δ; 14.0, 22.6, 25.8, 26.9, 28.5, 28.88, 28.91, 28.98, 29.05, 29.1, 29.2, 29.28, 29.3, 29.5, 29.60, 29.62, 29.7, 31.9, 32.1, 36.9, 44.1, 54.9, 62.5, 74.5, 98.5, 123.9, 129.3, 133.9, 136.3, 144.0, 144.1, 144.4, 174.0;

IR (neat) υ: 3299, 2918, 2849, 1578, 1558, 1297, 1260, 720 cm$^{-1}$;

LRMS (FAB) m/z 660 [M+H]$^+$ 682 [M+Na]$^+$;

HRMS (FAB) calcd for C$_{36}$H$_{61}$N$_5$O$_6$Na 682.4520 [M+Na]$^+$. found 682.4509.

Synthesis Example 7

Synthesis of (2S,3R)-(E)-3-hydroxy-14-((7-nitrobenzo[c][1,2,5]oxadiazole-4-yl)amino)-2-palmitamide tetradec-4-en-1-yl acetate (Compound 9)

Into a pyridine solution (600 μL) of the compound 8 (20 mg, 0.03 mmol) synthesized by the method of the Synthesis Example 6 described above, acetyl chloride (10 μL, 0.15 mmol) was added at −15° C., and the resultant mixture was stirred for one hour. Into the resultant reaction mixture, a saturated aqueous solution of sodium carbonate was added, and the product was extracted with dichloromethane. The organic layer was washed with 1N hydrochloric acid, and a saturated salt solution, and then the washed organic layer was dried over anhydrous sodium sulfate. The solvent was distilled off under reduced pressure, then the residue was purified by thin-layer chromatography (developer: CHCl$_3$/methanol (10/1)), and the compound 9 (17.5 mg, 83%) was obtained as an orange solid.

$^1$H NMR (CDCl$_3$, 400 MHz) δ; 0.88 (t, J=7.2 Hz, 3H), 1.21-1.43 (m, 34H), 1.47 (quin, J=7.2 Hz, 2H), 1.56 (br, 2H), 1.81 (quin, J=7.2 Hz, 2H), 2.03 (q, J=7.2 Hz, 2H), 2.07 (s, 3H), 2.77 (br, 1H), 3.49 (q, J=6.8 Hz, 2H), 4.13-4.27 (m, 3H), 4.32 (dd, J=11.2, 6.8 Hz, 2H), 5.47 (ddt, J=15.2, 6.8, 1.2 Hz, 1H), 5.74 (dt, J=15.6, 6.4 Hz, 1H), 5.88 (d, J=6.0 Hz, 1H), 6.17 (d, J=8.4 Hz, 1H), 6.45 (br, 1H), 8.50 (d, J=8.8 Hz, 1H);

$^{13}$C NMR (CDCl$_3$, 400 MHz) δ; 173.9, 171.3, 144.3, 143.9, 136.5, 134.4, 128.3, 73.3, 62.9, 53.3, 36.8, 32.1, 31.9, 29.67, 29.65, 29.64, 29.63, 29.61, 29.5, 29.35, 29.34, 29.33, 29.2, 29.19, 29.13, 29.0, 28.9, 28.83, 28.82, 25.7, 22.7, 20.9, 14.1;

IR (neat) υ: 3310, 2916, 2848, 1740, 1583, 1297, 1242, 1042, 721 cm$^{-1}$;

LRMS (FAB) m/z 702 [M+H]$^+$, 724 [M+Na]$^+$;

HRMS (FAB) calcd for C$_{38}$H$_{63}$N$_5$O$_7$Na 724.4625 [M+Na]$^+$. found 724.4613.

<Evaluation of Cytotoxicity of Ceramide Derivative (Alteration of Cell Shape)>

As to the compound 9 synthesized in the above, the cytotoxicity was evaluated as the effect on the change in cell morphology.

As the cultured cells, cells obtained by the culture of CHO cells, which is a cell strain derived from the ovary of hamster, in a Ham's F12 medium were used.

Firstly, the CHO cells were seeded into each well of a 24-well plate at 2×10$^4$ cells/well, and cultured in a Ham's F12(+) medium at 37° C. for one day. After that, in order to eliminate the influence of ceramide, sphingosine, and the like, medium exchange to a medium in which 0.1% BSA and 10 mM HEPES are added into a Ham's F12(−) medium which is a serum-free medium was performed, and in the presence of the compound 9 (10 μM), the culture was further performed for one day. Further, as a negative control, the same experiment was performed with the a NBD-C6-ceramide described in Non Patent Literature 1.

Figure 1:
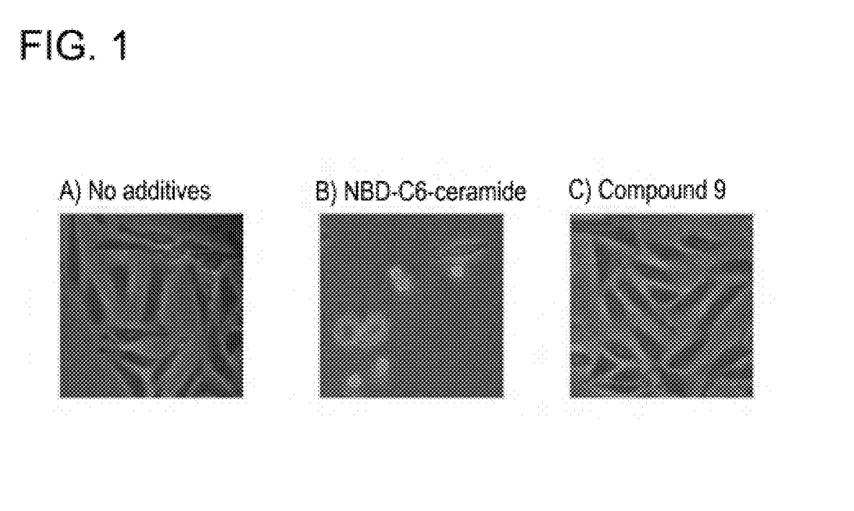
FIG. 1 is a set of pictures showing the results of the evaluation of the cytotoxicity for the compound 9 synthesized in the Synthesis Example, in Examples.

The results are shown in FIG. 1. As shown in FIG. 1, as compared with the results of the case (A) where a compound had not been added, in the case (B) where the NBD-C6-ceramide, which is known to cause cell dysfunction, had been added, the alteration of cell shapge (roundation) was observed. Herein, as shown in FIG. 1 (A), a CHO cell is a fibroblast-like cell in the form of an elongated flat, however, when a NBD-C6-ceramide is administered, the CHO cell becomes in the form that a foot does not extend from the cell due to the roundation. On the other hand, in the case (C) where the compound 9, which is a ceramide derivative according to the present invention, was administered, the roundation was not observed, and the fibroblast-like cell remained in the form of a flat.

<Evaluation of Cytotoxicity of Ceramide Derivative (Changes in Cell Number)>

Subsequently, as to the compound 9 synthesized in the above, the cytotoxicity was evaluated as the effect on the change in cell number.

Firstly, the CHO cells were seeded into each well of a 24-well plate at 1×10$^4$ cells/well, and cultured in a Ham's F12(+) medium at 37° C. for one day. The cell number one day after the culture was 1.26×10$^4$ cells/well. After that, medium exchange to a medium in which 0.1% BSA and 10 mM HEPES are added into a Ham's F12(−) medium which is a serum-free medium was performed, and in the presence of the compound 9 (10 μM), the culture was further performed for one day. Further, as a negative control, the same experiment was performed with the NBD-C6-ceramide described in Non Patent Literature 1. In addition, the same experiment was also performed for the case of no additives.

The results are shown in the following Table 1.

TABLE 1

| Before addition | | 12,600 cells/well | 100% |
|---|---|---|---|
| After addition (24 hours) | No additives | 21,400 ± 6400 cells/well | 170 ± 51% |
| | NBD-C6-ceramide | 9,690 ± 260 cells/well | 77 ± 2% |
| | Acetyl-C16-ceramide-NBD (compound 9) | 20,000 ± 4100 cells/well | 159 ± 33% |

As shown in Table 1, the cells were proliferated in the case of no additives, therefore, the cell number 24 hours after the culture had been increased to 170% on average as compared to that before the addition although there were variations. Further, even in the case where the compound 9 (10 μM) is present, the cell number was increased to 159% as in the case of no additives, and the cell proliferation equivalent to that in the case of no additives was observed without the loss of cells. On the other hand, in the presence of a NBD-C6-ceramide, the cell number was significantly decreased to 77%.

From this result, the ceramide derivative according to the present invention was indicated to be a compound which has extremely low cytotoxicity.

<Evaluation of Incorporation into Cell and Metabolism of Ceramide Derivative>

As to the compound 9 synthesized in the above, the incorporation into a cell and the metabolism were evaluated.

Firstly, the CHO cells were seeded into each well of a 24-well plate at 2×10$^4$ cells/well, and cultured in a Ham's F12(+) medium at 37° C. for one day. After that, medium exchange to a medium in which 0.1% BSA and 10 mM HEPES are added into a Ham's F12(−) medium which is a serum-free medium was performed, and the culture was further performed at 37° C. for 18 hours, then into which the compound 9 (10 μM) was added. After the addition, the resultant mixture was cultured at 37° C. for 1, 2, 6, 24, or 48 hours, and subjected to an assay. Further, as a negative control, the same experiment was performed with the NBD-C6-ceramide. Herein, ceramide, sphingosine, and the like are contained in the serum, and the incorporation and metabolism of these substances are constantly in progress. Therefore, in this experiment, firstly, the cells were cultured for 18 hours in a serum-free medium, and the incorporation and metabolism of a serum-derived compound were decreased, then the test compound was added, and thus an experimental system was constructed such that the pure incorporation and metabolism of the test compound itself can be measured.

As the assay, firstly, the incorporation of the ceramide derivative (compound 9) into a cell was evaluated. Specifically, cells that had been cultured for a predetermined time in the presence of the compound were washed twice with HBSS (Hank's Balanced Salt Solution: pH 7.4) containing 0.1% BSA and 10 mM HEPES, and then using a cell scraper and 250 μL of HBSS, the cells were detached from the wells. Into the cell extract thus obtained, 500 μL of chloroform, 500 μL of methanol, and 250 μL of water were added, and the cell extract was prepared in two-layer form of an organic layer and an aqueous layer. Further, since the ceramide derivative and other major sphingolipids are compounds that migrate to the organic layer, the cell extract in two-layer form was centrifuged for 10 minutes under the conditions of 3000 rpm at 4° C., and thus only the organic layer was isolated.

Subsequently, the obtained organic layer sample was added into a 96-well plate, and the fluorescence emission of the ceramide derivative was detected by using an image analyzer (LAS1000, manufactured by FUJIFILM Corporation).

The results are shown in A) and B) of FIG. 2. A) in FIG. 2 is a set of pictures taken by the image analyzer, and the portion where fluorescence is emitted is displayed in black. Further, B) in FIG. 2 is a graph plotted with the amount of incorporated compound [nmol/well] determined by a calibration curve method using the NBD-C6-ceramide as a standard reference material as the vertical axis, and the culture time as the horizontal axis. In addition, there were $8 \times 10^4$ cells per well. As can be understood from the results shown in A) and B) of FIG. 2, it has been proved that the amount of the NBD-C6-ceramide, which is a negative control, incorporated into a cell is decreased with the lapse of time, whereas the amount of the compound 9, which is a ceramide derivative according to the present invention, incorporated into a cell is increased with the lapse of time.

On the other hand, as another assay, the metabolism of the ceramide derivative (compound 9) was evaluated. Specifically, 20 μL of the organic layer sample thus obtained above was spotted on a TLC plate, and developed with a development solvent (1-butanol:acetic acid:water=3:1:1), then the intracellular metabolism of the sample was evaluated by using an image analyzer (LAS1000).

The results are shown in C) of FIG. 2 (NBD-C6-ceramide (negative control)), and D) of FIG. 2 (compound 9). As shown in C) of FIG. 2, the NBD-C6-ceramide was metabolized with the lapse of time, and it is estimated that the amount was decreased by half in 24 hours, and the majority became a degradation product that moves in a fraction other than the organic layer fractions (water layer fraction). Further, along with the loss of the NBD-C6-ceramide, the presence of other sphingolipids such as glucosylceramide, and sphingomyelin, which are metabolites, has been observed. For example, in 6 hours, 30% of the NBD-C6-ceramide became a metabolite. On the other hand, as shown in D) of FIG. 2, in the compound 9, the metabolite in 6 hours was around 10% of the total. Even in 48 hours, nearly 90% of the NBD-C6-ceramide was metabolized, however, in the compound 9, 70% or more of the compound 9 remained as it is without being metabolized. In other words, the NBD-C6-ceramide is metabolized (degraded) in a cell when in contact with a cell for a long time, and thus the NBD-C6-ceramide cannot remain as the ceramide for a long time. On the other hand, in a ceramide derivative according to the present invention such as the compound 9, the amount of the incorporated compound is small in a short time, and it was confirmed that the ceramide derivative is a compound that can remain as it is as the ceramide form even in 48 hours.

Figure 2A:
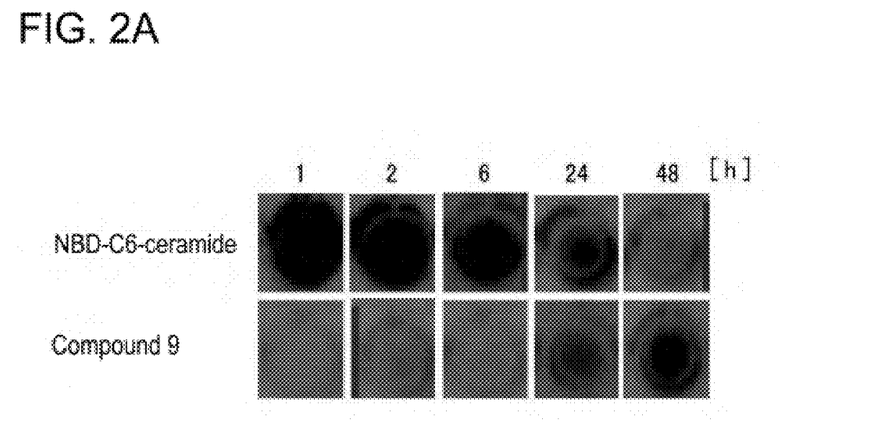
FIG. 2A is a set of pictures showing the results of the evaluation of the incorporation into a cell for the compound 9 synthesized in the Synthesis Example, in Examples, in comparison with the NBD-C6-ceramide (negative control)
Figure 2B:
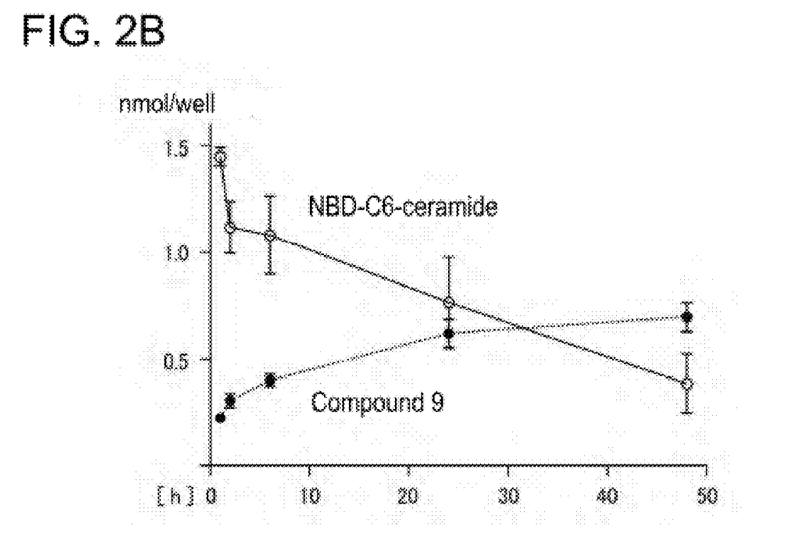
FIG. 2B is a graph showing the results of the evaluation of the incorporation into a cell for the compound 9 synthesized in the Synthesis Example, in Examples, in comparison with the NBD-C6-ceramide (negative control)
Figure 2C:
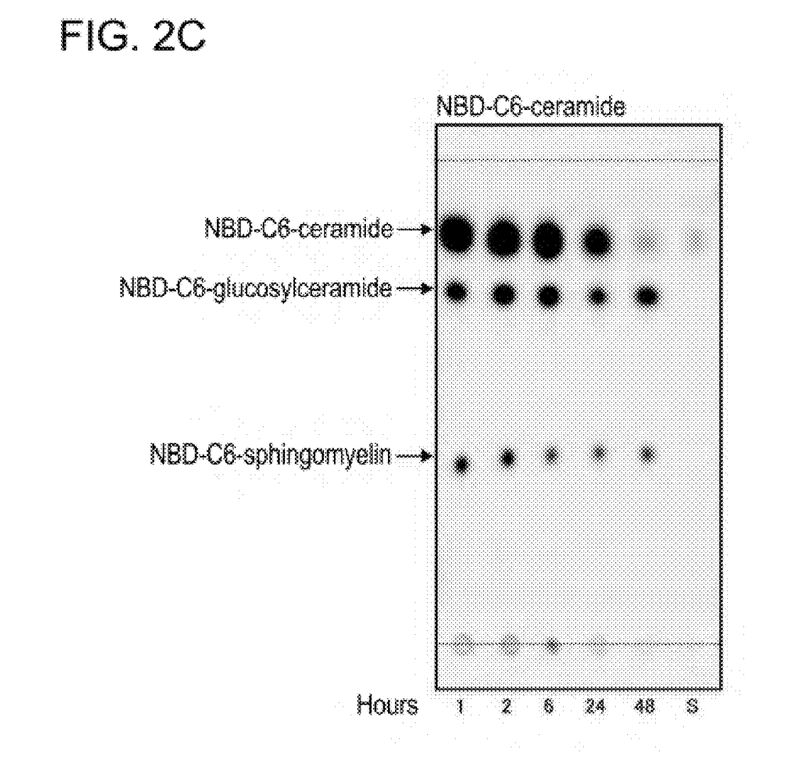
FIG. 2C is a picture showing the results of the evaluation of the metabolism by thin-layer chromatography (TLC) for the NBD-C6-ceramide (negative control), in Examples.
Figure 2D:
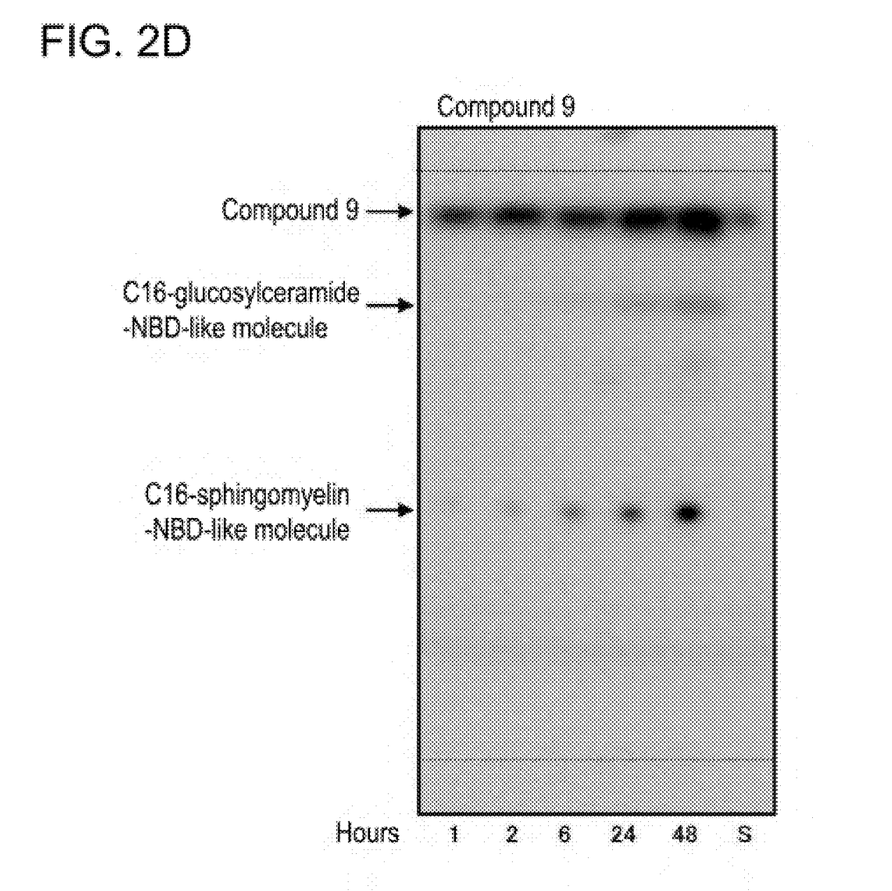
FIG. 2D is a picture showing the results of the evaluation of the metabolism by TLC for the compound 9 synthesized in the Synthesis Example, in Examples.
Figure 2E:
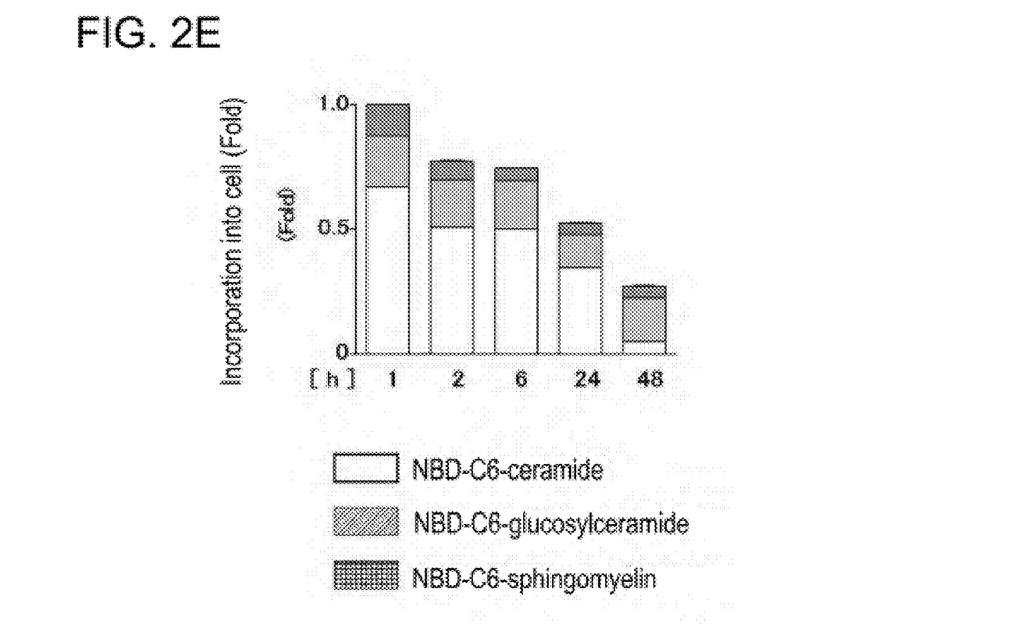
FIG. 2E is a graph obtained by the numerical conversion of the results of the evaluation of the metabolism by TLC for the NBD-C6-ceramide (negative control), in Examples.
Figure 2F:
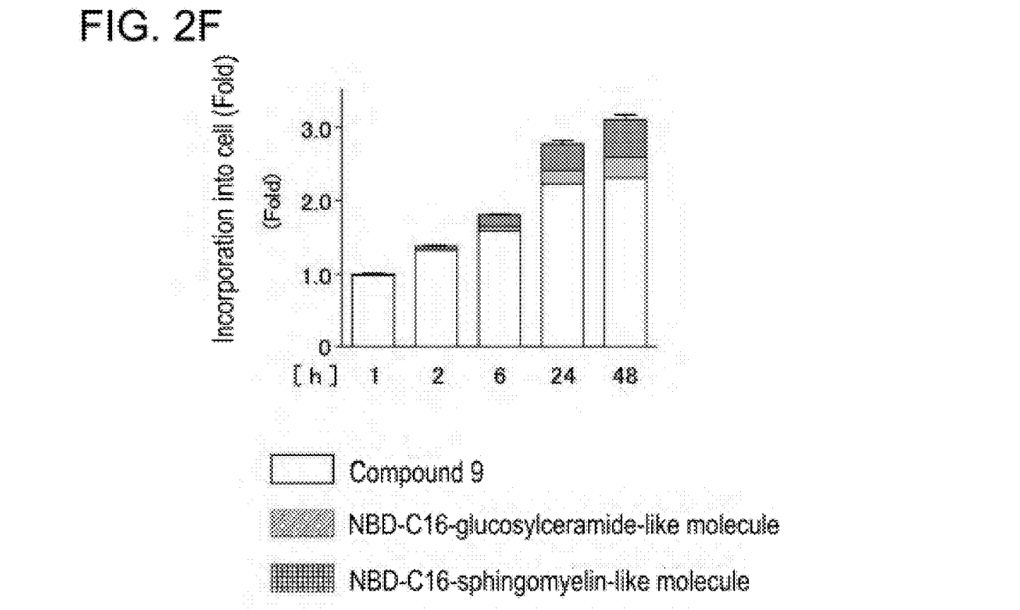
FIG. 2F is a graph obtained by the numerical conversion of the results of the evaluation of the metabolism by TLC for the compound 9 synthesized in the Synthesis Example, in Examples.

Further, by using a free software (Image J), the abundance of each metabolite was converted into a numerical value. The results are shown in E) of FIG. 2 (NBD-C6-ceramide (negative control)), and F) of FIG. 2 (compound 9). In the meantime, the numerical value of each amount of C16-glucosyl-ceramide-NBD-like molecules and C16-sphingomyelin-NBD-like molecules was determined from the mobility in the TLC.

<Evaluation of the Localization Performance of Ceramide Derivative to the Golgi Apparatus>

It was evaluated whether or not the localization of the compound 9 into a cell is really due to the localization to the Golgi apparatus. Specifically, BODIPY-TR-Ceramide (Cat D-7540 Red manufactured by Molecular Probes), which is another Golgi marker known to be difficult to be metabolized, was added together with the compound 9 into a cell, and the observation was performed by using a confocal laser scanning microscope.

Firstly, the CHO cells were seeded into each well of a 24-well plate at $0.5 \times 10^4$ cells/well, and cultured in a Ham's F12(+) medium at 37° C. for two days. After that, medium exchange to HBSS (Hank's Balanced Salt Solution: pH 7.4) (−) containing 0.1% BSA and 10 mM HEPES was performed, and the compound 9 (1 μM) was further added, and the resultant mixture was cultured at 37° C. for 1.5 hours. Next, the cells were washed twice with HBSS containing 0.1% BSA and 10 mM HEPES, and into which BODIPY-TR-Ceramide (5 μM) was added, then in the same medium, the resultant mixture was further cultured for 30 minutes. After completion of the culture, the cells were washed twice in the same manner as described above, and then the fluorescence emission from the cells was observed. The washing of cells before the observation is for the elimination of the noise due to the detection of the emission from the compound remained in the medium. Further, the same experiment was performed by using the NBD-C6-ceramide as a negative control. In addition, the time course of the cell culture and compound addition is the one recommended by data sheets or previous reports as the time course in which BODIPY-TR-Ceramide can be detected more sensitively. The observation was performed by using a confocal laser scanning microscope, and the measurement of the fluorescence emission from the BODIPY-TR-Ceramide was performed at the maximum excitation wavelength of 598 nm, and the maximum fluorescence wavelength of 617 nm, to measure the "red". Further, the measurement of the fluorescence emission from the compound 9 or the NBD-C6-ceramide (negative control) was performed at the maximum excitation wavelength of 489 nm, and the maximum fluorescence wavelength of 508 nm, to measure the "green".

Figure 3:
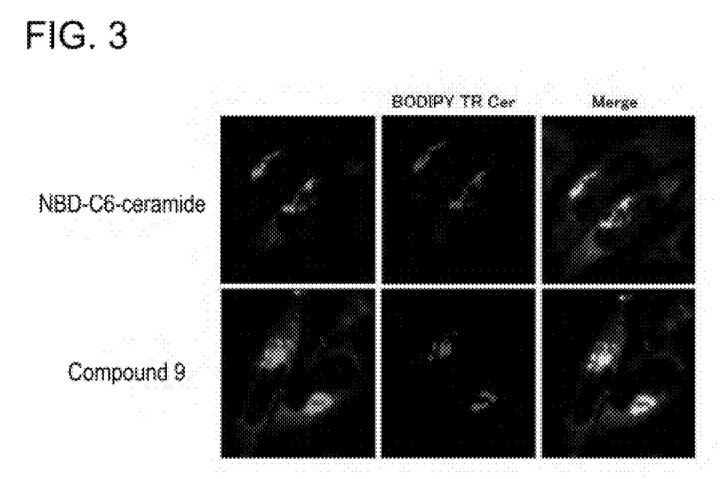
FIG. 3 is a set of pictures showing the results of the evaluation of the localization performance to the Golgi apparatus for the compound 9 synthesized in the Synthesis Example, in Examples, in comparison with the NBD-C6-ceramide (negative control)

The results are shown in FIG. 3. Among the pictures shown in FIG. 3, each of the left pictures is a picture obtained from the observation of the emission of fluorescence (green) derived from the NBD-C6-ceramide or the compound 9, the each of middle pictures is a picture obtained from the observation of the emission of fluorescence (red) derived from the BODIPY-TR-Ceramide, and each of the right pictures is a picture obtained by merging the left one and the middle one. In also this experiment, it was observed that the NBD-C6-ceramide, which is a conventional Golgi marker, was co-localized with the BODIPY-TR-Ceramide, which is also a Golgi marker (a picture in the upper right of FIG. 3). As to the NBD-C6-ceramide, it has been reported that even 30 minutes after the addition into a cell, or even in the case where the NBD-C6-ceramide is metabolized to sphingomyelin or glucosylceramide two hours later, the resultant remains in the Golgi apparatus (J Cell Biol. 1985 January; 100 (1): 27-34). By the study of the inventors, similar results have been also confirmed. On the other hand, also as to the ceramide derivative according to the present invention (compound 9), it was observed that the ceramide derivative is co-localized with the BODIPY-TR-Ceramide (a picture in the bottom right of FIG. 3). From the above, it was confirmed that the compound 9 can be used as a Golgi apparatus-labeling fluorescent probe.

Subsequently, it was evaluated whether or not the localization of the compound 9 in the Golgi apparatus can be maintained over a long period of time. Specifically, by the method similar to that described above, the compound 9 or the NBD-C6-ceramide (negative control) (each of both is in 1 μM) was added, then the resultant mixture was cultured at 37° C. for 1, 2, 6, 24, or 48 hours, and the fluorescence (green) derived from the compound was observed.

Figure 4:
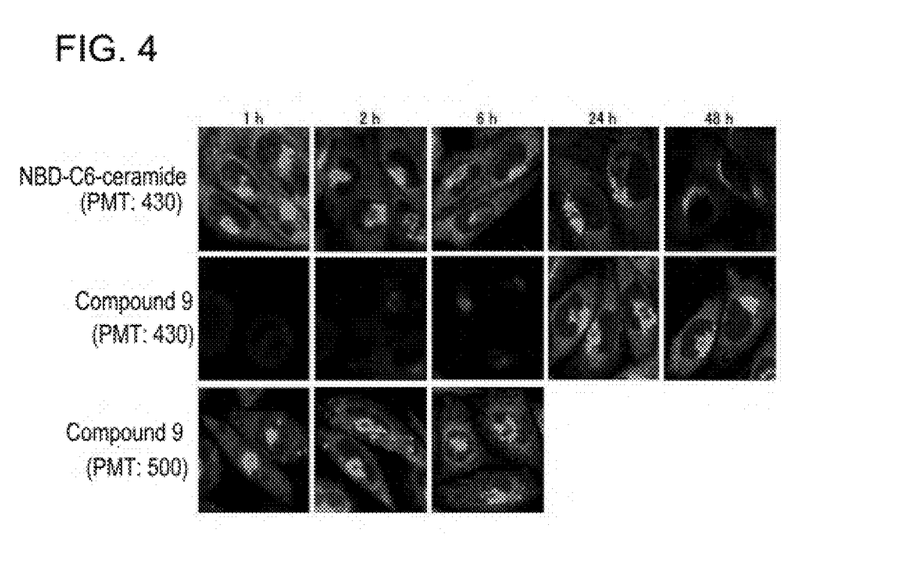
FIG. 4 is a set of pictures showing the results of the evaluation of the changes in the localization performance to the Golgi apparatus over time for the compound 9 synthesized in the Synthesis Example, in Examples, in comparison with the NBD-C6-ceramide (negative control).

The results are shown in FIG. 4. The upper part of FIG. 4 is a set of pictures showing the results of the observation for the NBD-C6-ceramide (negative control), the pictures were taken by using a photomultiplier tube PMT:430. The middle part of FIG. 4 is a set of pictures showing the results of the observation for the compound 9, the pictures were taken by using a photomultiplier tube PMT:430. The lower part of FIG. 4 is a set of pictures showing the results of the observation for the compound. 9, the pictures were taken by using a photomultiplier tube PMT:500. At this point, the expression of "430" or "500" means detection sensitivity (size of the energy required to detect the emission derived from a compound), and the smaller the value, the higher the sensitivity. Therefore, it means that in the case where the detection cannot be performed if the value is not increased., the absolute amount of the emission is small (that is, the abundance of fluorescent compound in a cell is small).

From the results shown in the upper part of FIG. 4, the fluorescence intensity of the NBD-C6-ceramide, which is a negative control, is attenuated with the lapse of time, and thus it is understood that the localization to the Golgi apparatus is decreased over time. It can be considered that the results support the results of intracellular metabolism shown in FIGS. 2A to 2C, and 2E.

On the other hand, as to the compound 9, as shown in the middle part and lower part of FIG. 4, in the initial stage of the addition, the detection of the emission of fluorescence cannot be performed if the sensitivity of detection apparatus is not increased, however, the emission intensity is gradually increased with the lapse of time, and 24 hours after the addition, the emission of fluorescence could be sufficiently confirmed even if the detection sensitivity is decreased. These results also support the results of intracellular metabolism shown in FIGS. 2A to 2B, 2D, and 2F.

From the above, it was shown that the ceramide derivative according to the present invention, for example, when used as a Golgi apparatus-labeling fluorescent probe, exerts an extremely significant effect in which the cytotoxicity is low and the intracellular stability is excellent.

The invention claimed is:

1. A ceramide derivative represented by the following Chemical formula 1:

[Chemical formula 1]

wherein $R_1$ is an alkyl group having 1 to 12 carbon atoms, $R_2$ is an alkyl group having 1 to 20 carbon atoms, and n is an integer of 1 to 20.

2. The ceramide derivative according to claim 1, represented by the following Chemical formula 2:

[Chemical formula 2]

3. The ceramide derivative according to claim 1, wherein $R_1$ is an alkyl group having 1 to 4 carbon atoms.

4. The ceramide derivative according to claim 1, wherein $R_2$ is an alkyl group having 5 to 15 carbon atoms.

5. The ceramide derivative according to claim 1, wherein n is an integer of 7 to 11.

6. A ceramide derivative, represented by the following Chemical formula 3:

[Chemical formula 3]

7. A Golgi apparatus-labeling fluorescent probe, comprising the ceramide derivative according to claim 1.

8. A method of identifying an existing site of Golgi apparatus in a test cell, comprising:
   contacting the Golgi apparatus-labeling fluorescent probe according to claim 7 with a test cell; and
   measuring a fluorescence signal emitted by the fluorescent probe.

9. A method of measuring presence or absence, or a degree of localization of a test compound to the Golgi apparatus in a test cell, comprising:
   contacting the Golgi apparatus-labeling fluorescent probe according to claim 7 with a test cell;
   measuring a fluorescence signal emitted by the fluorescent probe;
   bringing a fluoresceinated test compound into contact with the test cell; and
   measuring a fluorescence signal emitted by the test compound.

10. The ceramide derivative according to claim 2, wherein $R_1$ is an alkyl group having 1 to 4 carbon atoms.

11. The ceramide derivative according to claim 2, wherein $R_2$ is an alkyl group having 5 to 15 carbon atoms.

12. The ceramide derivative according to claim 2, wherein n is an integer of 7 to 11.

13. A Golgi apparatus-labeling fluorescent probe, comprising the ceramide derivative according to claim 2.

14. A method of identifying an existing site of Golgi apparatus in a test cell, comprising:
   contacting the Golgi apparatus-labeling fluorescent probe according to claim 13 with a test cell; and
   measuring a fluorescence signal emitted by the fluorescent probe.

15. A method of measuring presence or absence, or a degree of localization of a test compound to the Golgi apparatus in a test cell, comprising:
   contacting the Golgi apparatus-labeling fluorescent probe according to claim 13 with a test cell;
   measuring a fluorescence signal emitted by the fluorescent probe;
   bringing a fluoresceinated test compound into contact with the test cell; and
   measuring a fluorescence signal emitted by the test compound.

16. A Golgi apparatus-labeling fluorescent probe, comprising the ceramide derivative according to claim 6.

17. A method of identifying an existing site of Golgi apparatus in a test cell, comprising:
   contacting the Golgi apparatus-labeling fluorescent probe according to claim 16 with a test cell; and
   measuring a fluorescence signal emitted by the fluorescent probe.

18. A method of measuring presence or absence, or a degree of localization of a test compound to the Golgi apparatus in a test cell, comprising:
   contacting the Golgi apparatus-labeling fluorescent probe according to claim 16 with a test cell;
   measuring a fluorescence signal emitted by the fluorescent probe;
   bringing a fluoresceinated test compound into contact with the test cell; and
   measuring a fluorescence signal emitted by the test compound.

* * * * *